United States Patent [19]
Wang

[11] 3,969,076
[45] July 13, 1976

[54] METHOD FOR THE ANALYSIS OF IONIC SURFACTANTS
[75] Inventor: Lawrence K. Wang, Buffalo, N.Y.
[73] Assignee: Calspan Corporation, Buffalo, N.Y.
[22] Filed: May 27, 1975
[21] Appl. No.: 580,646

Related U.S. Application Data
[63] Continuation of Ser. No. 385,775, Aug. 6, 1973, abandoned.

[52] U.S. Cl. .............................. 23/230 R; 23/230 M; 252/408
[51] Int. Cl.² ................. G01N 31/00; G01N 31/16; G01N 31/22
[58] Field of Search .................... 23/230 R, 230 M; 252/408

[56] References Cited
UNITED STATES PATENTS
3,725,006  4/1973  Brandstrom...................... 23/230 R OTHER PUBLICATIONS
Scott, George V., Spectrophotometric Determination of Cationic Surfactants with Orange II, Analical Chemistry April, 1968, pp. 768–773.
Swisher, R. D., Surfactant Biodegradation, Marcel Dekker Inc., New York, 1970, pp. 50–54.

Primary Examiner—Morris O. Wolk
Assistant Examiner—Dale Lovercheck
Attorney, Agent, or Firm—Allen J. Jaffe

[57] ABSTRACT

A method for analyzing sea water, raw water supplies, domestic sewage or industrial wastes for the presence of ionic surfactants, such as detergents, and the determination of whether surfactant is anionic or cationic. The method employs the back titration of a sample to which an excess of cationic surfactant has been added.

5 Claims, No Drawings

METHOD FOR THE ANALYSIS OF IONIC SURFACTANTS

This is a continuation of application Ser. No. 385,775, filed Aug. 6, 1973, now abandoned.

Presently employed synthetic detergents contain surface active agents or surfactants such as linear alkylate sulfonate (LAS). LAS, an anionic detergent, is an alkyl aryl sulfonate whose structure is made up of a straight-chain alkyl group, a benzene ring, and a sulfonate. The wide usage of LAS type detergents in both domestic and industrial applications, together with their toxicity, necessitate the monitoring of waste water effluents for the presence of anionic surfactants.

The methylene blue method and the carbon adsorption method are the standard methods for the determination of anionic detergents in aqueous solutions. Difficulties arise, however, because the methylene blue method is not applicable to the measurement of anionic detergent in saline waters, and the carbon adsorption method is applicable to the measurement of detergent in raw-water samples only (i.e., not to detergents in sewage or industrial wastes).

It is an object of this invention to provide an improved method for the analysis of ionic surfactants in aqueous solution.

It is another object of this invention to provide a method suitable for the analysis of both anionic and cationic detergents.

It is a further object of this invention to provide a method for the determination of ionic surfactants in sea water. These objects, and others as will become apparent hereinafter, are accomplished by the present invention.

The method of this invention is suitable for the analysis and detection of anionic and cationic detergents, pesticides, organic electrolytes, wetting agents, flotation agents, or any other ionic surface active agents in aqueous solution. Advantages of the method of the present invention over standard methods such as the methylene blue method and the carbon adsorption method include its suitability for saline water analysis, the use of a single test to quantitatively measure the detergent/surfactant content and to indicate whether it is anionic or cationic, and a rapid, simple procedure which does not require expensive equipment and which is suitable for use in the field.

According to this invention, the water sample is treated first with a known amount of a nonaromatic quaternary ammonium salt to react with an equivalent amount of anionic detergent forming a complex compound between the quarternary ammonium ions and the linear alkylate sulfonate radical. By adjusting the solution to pH=3.0 with a suitable buffer, the excess cationic quarternary ammonium reagent is made partially soluble in an added chloroform layer, giving rise to a yellow color in the organic liquid phase. This water-chloroform two-phase mixture is then titrated with a standard sodium tetraphenylboron reagent with intermittent shaking to insure equilibrium between the chloroform and the aqueous phases. As the final traces of the quarternary ammonium reagent are removed from the chloroform layer and complexed with the tetraphenylboron radical, the yellow color in the chloroform layer will disappear, indicating an equivalent point of the titration. The actual concentration of ionic detergent or surfactant is given by the difference between the amount of the quarternary ammonium compound added to the sample and that found by titration with sodium tetraphenylboron.

REAGENTS

1. Stock sodium tetraphenylboron (STPB) solution: dissolve 3.50 grams of STPB in one liter of distilled water, adjust the pH value to a value betwen 9 and 10 with sodium hydroxide and store the solution in an amber glass bottle.

2. Standard sodium tetraphenylboron (STPB) solution: dilute 10.00 ml of stock STPB solution into one liter of distilled water to obtain a concentration of 35.0 mg/l. This is the suggested titrant concentration for the titration of cationic detergent concentration in the range of 0-30 mg/l. Other proper STPB concentrations can be prepared depending upon the concentration range of cationic detergent.

3. Stock linear alkylate sulfonate (LAS) solution: weigh an amount of the reference material equal to 1.000 g LAS on a 100% active basis, dissolve in distilled water and dilute to one liter to obtain a concentration of 1.00 ml = 1.00 mg LAS. This solution should be stored in a refrigerator to minimize biodegradation.

4. Standard linear alkylate sulfonate (LAS) solution: dilute 50.00 ml of stock LAS solution to one liter with distilled water to obtain a concentration of 1.00 ml = 50.0 $\mu$g LAS.

5. Stock cetyl dimethyl benzyl ammonium chloride (CDBAC) solution: weigh an amount of the reference material equal to 1.000 g CDBAC on a 100% active basis, dissolve in distilled water and dilute to one liter to obtain a concentration of 1.00 ml = 1.00 mg CDBAC. This solution should be stored in a refrigerator to minimize biodegradation.

6. Standard cetyl dimethyl benzyl ammonium chloride (CDBAC) solution: dilute 50.00 ml of stock CDBAC solution to one liter with distilled water to obtain a concentration of 1.00 ml = 50 $\mu$g CDBAC.

7. Citric acid, 0.5 M.

8. Disodium hydrogen orthophosphate, 0.2 M.

9. Methyl orange solution, 0.10%.

10. Chloroform.

11. Buffer solution: mix 200 ml of 0.5 M citric acid and 200 ml of 0.2 M disodium hydrogen orthophosphate together.

ANALYSIS OF ANIONIC OR CATIONIC DETERGENTS

1. Preparation of calibration curve "A": prepare a series of ten 300-ml separatory funnels with 0, 2, 4, 6, 8, 10, 15, 20, 25 and 30 ml of the standard LAS solution. Add 30 ml of the standard CDBAC solution to each funnel and add sufficient distilled water to make the total volume 60 ml in each separatory funnel. To each separatory funnel add 5 ml of buffer solution, 5 drops of metyl orange solution and 30 ml of chloroform, stopper and shake vigorously. Titrate each solution with the standard STPB solution by adding small amounts, restoppering and shaking. Continue the titration until the yellow color in the chloroform layer becomes completely colorless. Plot a calibration curve of $\mu$g LAS versus ml of standard STPB titrant.

2. Preparation of calibration curve "B": prepare a series of ten 300 ml separatory funnels with 0, 2, 4, 6, 8, 10, 15, 20, 25 and 30 ml of the standard CDBAC solution. Add 30 ml of the standard CDBAC solution to each funnel and add sufficient distilled water to make the total volume 60 ml in each separatory funnel. To each separatory funnel add 5 ml of buffer solution, 5 drops of methyl orange solution and 30 ml of chloroform, stopper and shake vigorously. Titrate each solution with the standard STPB solution by adding small amounts, restoppering and shaking. Continue the titration until the yellow color in the chloroform layer becomes completely colorless. Plot a calibration curve of $\mu$g CDBAC (counting initially added CDBAC from 0, 2, 4 ... to 30 ml only) versus ml of standard STPB titrant.

3. Pipette an aliquot amount of the detergent sample into a separatory funnel. Dilute to 30 ml with distilled water and add 30 ml of the standard CDBAC solution to the separatory funnel.

4. Add 5 ml of buffer solution, 5 drops of methyl orange solution and 30 ml of chloroform to the separatory funnel, stopper and shake vigorously.

5. Titrate this solution in the separatory funnel with standard STPB solution by adding small amounts, restoppering and shaking.

6. Continue the titration until the yellow color in the chloroform layer becomes completely colorless. Record the ml of standard STPB solution required for titration.

7. For an unknown sample, if the ml of standard STPB solution required for titrating the sample is less than that for titrating the blank sample (i.e., 30 ml distilled water plus 30 ml standard CDBAC solution) the detergent is anionic, whereas, if the ml of standard STPB solution required for titrating the sample is more than that for titrating the blank sample the detergent is cationic. For an anionic detergent read $\mu$g LAS present in the sample from the calibration curve "A" and calculate:

mg/l total apparent LAS = $\mu$g LAS/ml sample.

For a cationic detergent read $\mu$g CDBAC present in the sample from the calibration curve "B" and calculate:

mg/l total apparent CDBAC = $\mu$g CDBAC/ml sample.

In the practice of the method of the present invention other pure cationic surface active agents can also be used to replace the cetyl dimethyl benzyl ammonium chloride (CDBAC) such as cetyl trimethyl ammonium bromide, cetyl dimethyl ethyl ammonium bromide, cetyl pyridinium chloride, myristyl dimethyl benzyl ammonium chloride, alkyl dimethyl dichlorobenzyl ammonium chloride, myristy trimethyl ammonium bromide, alkenyl dimethyl ethyl ammonium bromide, stearyl dimethyl benzyl ammonium chloride, alkyl dimethyl benzyl ammonium chloride, etc. Additionally, alkyl benzene sulfonate, or any other anionic detergents or surfactants, can also be used to replace the linear alkylate sulfonate as the detergent standard and the volumes and concentrations of the reagents may be varied.

Although the preferred method of practicing the present invention has been described, other changes will occur to those skilled in the art. It is therefore intended that the scope of the present invention is to be limited only by the scope of the appended claims.

I claim:

1. A method for the analysis of ionic surfactants present in an aqueous solution including the steps of:
   obtaining a known volume sample of the aqueous solution to be tested;
   adding a standard, cationic, nonaromatic quarternary ammonia solution to the sample in a known amount sufficient to ensure a cationic character to the sample independent of its original condition;
   adding buffer solution, indicator and chloroform to the sample and mixing therewith to form a water-chloroform two phase mixture; and
   titrating the sample with a standard solution of sodium tetraphenylboron, whereby the actual concentration of ionic surfactant is given by the difference between the amount of quarternary ammonia compound added to the sample and that found by titration with the standard solution of sodium tetraphenylboron.

2. The method of claim 1 wherein said indicator is methyl orange solution.

3. The method of claim 1 wherein said buffer solution is a mixture of citric acid and disodium hydrogen orthophosphate.

4. The method of claim 1 wherein said quarternary ammonia solution is cetyl dimethyl benzyl ammonium chloride solution.

5. The method of claim 4 wherein said indicator is methyl orange solution and said buffer solution is a mixture of citric acid and disodium hydrogen orthophosphate.

* * * * *